United States Patent [19]
Khutoryansky et al.

[11] Patent Number: 5,572,567
[45] Date of Patent: Nov. 5, 1996

[54] UNIVERSAL RADIOGRAPHIC ROOM

[75] Inventors: Oscar Khutoryansky; Dennis Bleser; Allan Kojro, all of Glenview; Thomas Simak, Warrenville; Thomas Rosevear, Forest Park, all of Ill.

[73] Assignee: Continental X-Ray Corp., Broadview, Ill.

[21] Appl. No.: 351,617

[22] Filed: Dec. 8, 1994

[51] Int. Cl.⁶ .................................................... H05G 1/02
[52] U.S. Cl. ........................... 378/197; 378/177; 378/195
[58] Field of Search ..................................... 378/196, 197, 378/193, 195, 198, 204, 208, 209, 167, 174, 177, 181

[56] References Cited

U.S. PATENT DOCUMENTS

| | | | |
|---|---|---|---|
| 4,082,955 | 4/1978 | Sell | 250/445 T |
| 4,087,694 | 5/1978 | Hellstrom et al. | 250/455 T |
| 4,095,110 | 6/1978 | Bunch | 250/445 T |
| 4,145,613 | 3/1979 | Bunch | 250/445 T |
| 4,211,927 | 7/1980 | Hellstrom et al. | 250/445 T |
| 4,315,156 | 2/1982 | Sell | 250/445 T |
| 4,340,816 | 7/1982 | Schott | 250/445 T |
| 4,450,575 | 5/1984 | Mueller | 378/26 |
| 4,762,999 | 8/1988 | Saotome et al. | 250/327.2 |
| 4,807,273 | 2/1989 | Haendle | 378/197 |
| 4,882,489 | 11/1989 | Saotome et al. | 250/327.2 |
| 5,023,899 | 6/1991 | Ohlson | 378/197 X |
| 5,048,070 | 9/1991 | Maehama et al. | 378/197 |
| 5,177,778 | 1/1993 | Tsurumaki et al. | 378/197 X |

FOREIGN PATENT DOCUMENTS

| | | |
|---|---|---|
| 0686022 | 2/1940 | Germany . |
| 2741673 | 3/1978 | Germany . |

OTHER PUBLICATIONS

Siemens Medical Systems, Inc. Equipment Pricebook (Edition Oct. 1, 1992); cover page, 10, 16 & 18.

*Primary Examiner*—David P. Porta
*Attorney, Agent, or Firm*—Laff, Whitesel, Conte & Saret, Ltd.

[57] ABSTRACT

A universal radiographic apparatus that allows an operator to select between conventional radiographic mode and linear tomographic mode. In conventional radiographic mode of operation, several automatic modes are provided. An x-ray tube mounted to a tube crane positioned above an elevating table can be accurately controlled in longitudinal and vertical movement, as well as in x-ray tube angulation. In linear tomographic mode, a table bucky is moved laterally in opposition to movement of the tube crane, with angulation keeping the tube aimed at the bucky. In conventional radiographic mode, the system supports an auto bucky mode, where the table bucky automatically tracks tubecrane motion, or an auto table mode, where the tube crane tracks table vertical motion to maintain a fixed SID. In an auto wall mode, the tube crane tracks vertical movement of an associated wall bucky.

56 Claims, 8 Drawing Sheets ns 5,572,567

UNIVERSAL RADIOGRAPHIC ROOM

FIELD OF THE INVENTION

This invention relates generally to radiographic procedures, and in particular to a universal room for practicing radiographic procedure, and is more particularly directed toward a universal room that can be automatically converted for different types of examinations by selecting an appropriate mode of operation.

BACKGROUND OF THE INVENTION

The nature of conventional radiographic examination is well-known. Oftentimes, an image of particular interest is partially (or even completely) obscured by the shadows cast by adjacent anatomical structures.

Relief from this shadowing phenomenon can sometimes be obtained through the use of body section radiography, or tomography as it is commonly known. In tomography, structures that overlie or underlie the region of interest can be blurred out, while structures of interest are left with sharply defined boundaries. Linear tomography, where both the X-ray tube and X-ray film are constrained to straight-line motion, is perhaps the most common and easiest to practice variant of tomography.

Of course, many practitioners find both conventional radiographic techniques and linear tomography useful in diagnosis. However, the equipment presently available for conventional radiography is not generally compatible with the linear tomography process. Separate equipment designed solely for tomographic use is generally very expensive, and occupies a great deal of space that is often at a premium at the practitioner's site.

While there are examples of radiographic equipment that purport to be convertible from one mode to another, these are very costly, and lack features that would make them appealing to the average practitioner. Accordingly, a need arises for a universal radiographic room that provides desirable features in a compact arrangement and at a reasonable cost, and that facilitates the use of both conventional radiographic processes and linear tomographic examination.

SUMMARY OF THE INVENTION

These needs and others are satisfied by the universal radiographic room of the present invention, in which an x-ray generator equipped with a generator control that selects between conventional radiographic and linear tomographic modes of operation is provided. The universal radiographic room includes a tube mounting means for supporting the x-ray tube, the tube mounting means including longitudinal, lateral, vertical, and angulation mechanisms and associated position sensors. The universal radiographic room further includes an examining table with a table bucky that is equipped with a longitudinal drive mechanism and associated position sensor, and a wall bucky with an associated position sensor. A multi-axis motor controller operates the components of the system with the mode of operation being selected on the universal control panel.

In one embodiment, the examining table is equipped with an elevating feature that enables use of an automatic table mode of operation. In this mode, the tube follows vertical position of the table to maintain a predetermined source-image distance.

DESCRIPTION OF A PREFERRED EMBODIMENT

In accordance with the present invention, a universal radiographic room provides the capability to conduct conventional radiographic examinations or linear tomographic examinations using a relatively economical and compact arrangement that incorporates many features particularly attractive to the practitioner. The invention can best be understood with reference to the accompanying drawing figures.

Figure 1:
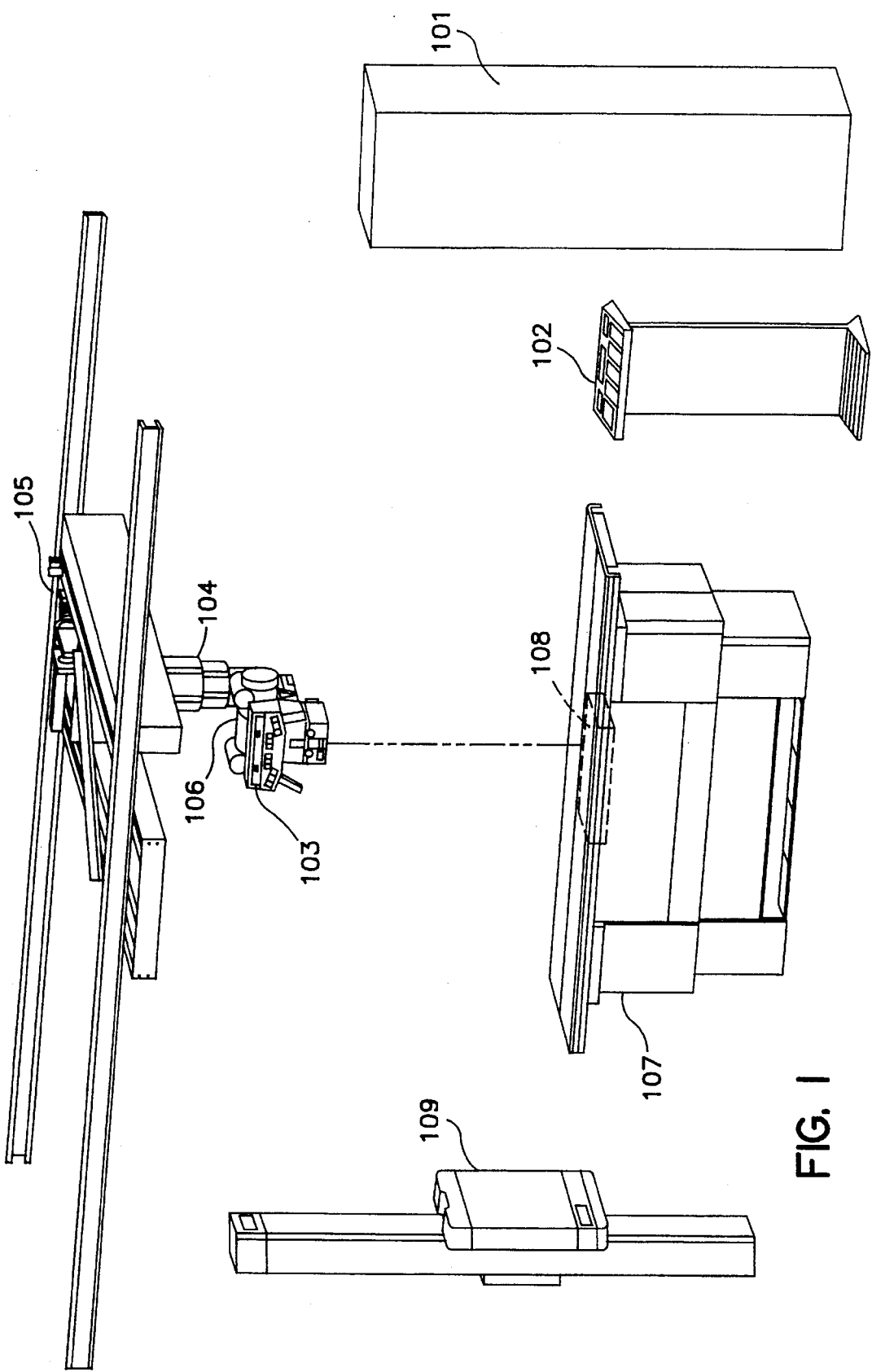
FIG. 1 is a perspective view, on a reduced scale, of a radiographic room in accordance with the present invention.

The following description is directed toward a universal room for radiographic studies that can be automatically converted for different types of examinations by selecting an appropriate mode of operation. The specific equipment that will be discussed in detail in the following sections is illustrated in FIG. 1, and includes an x-ray generator 101 and generator control 102 with a universal control panel 103 through which an operator can select radiographic (table or wall) or tomographic modes of operation, as well as automatic or manual modes of operation; a tubecrane 104 (or tubestand) with longitudinal and vertical drivers 105, x-ray tube angulation mechanisms and position sensors 106; an elevating table 107 with a table bucky 108, equipped with a longitudinal drive mechanism and position sensor, as well as a vertical position sensor; a wall bucky 109 with a position sensor; and a multi-axis motor controller.

The system is designed in such a way as to eliminate mechanical coupling between system components. The focal planes for linear tomography are selected electronically so that a fulcrum tower is not required. All motions of system components are synchronized in dependence upon the tomographic technique selected by the operator.

Figure 2:
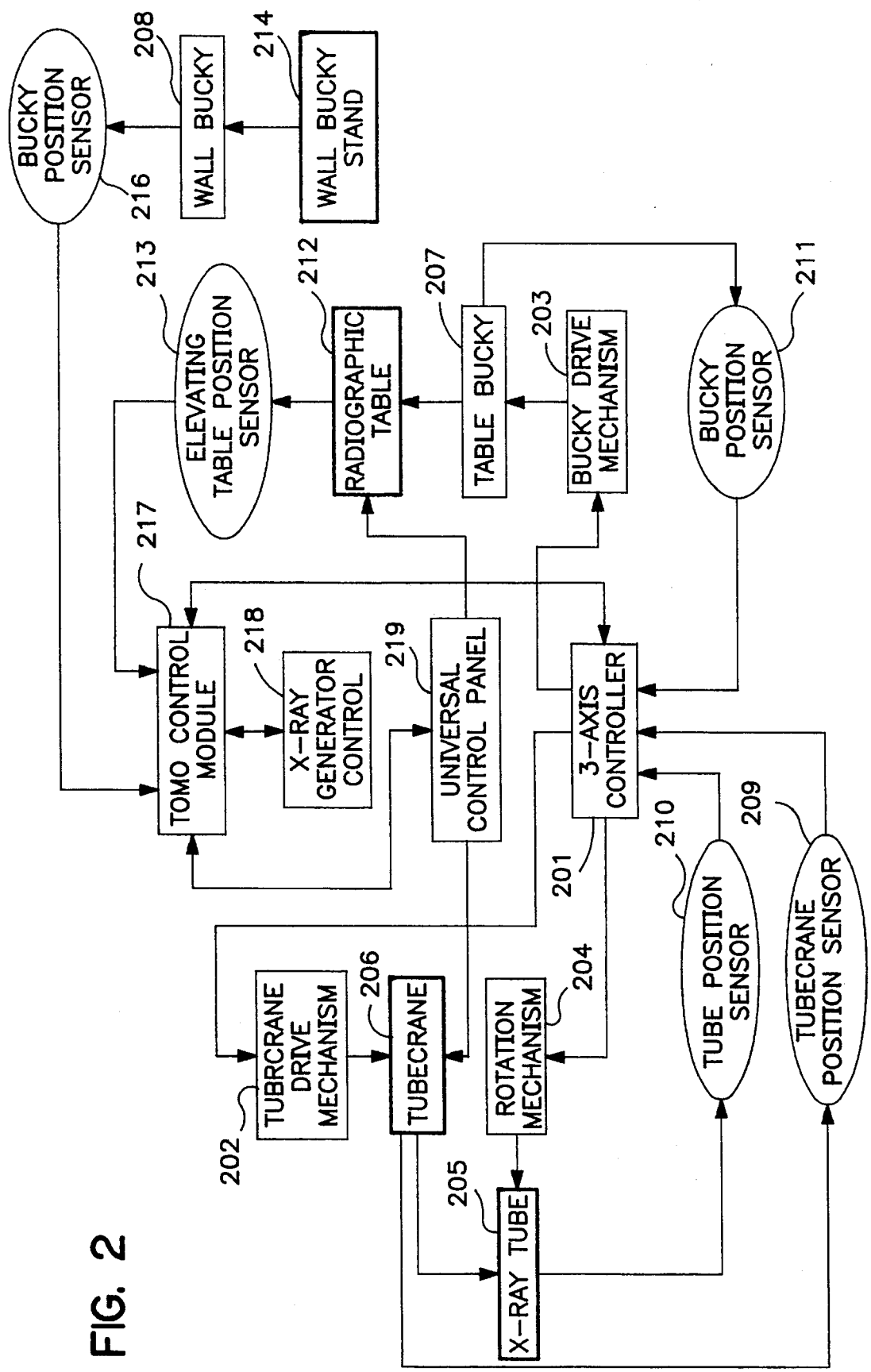
FIG. 2 is a block diagram representation of system components.

FIG. 2 is a block diagram illustrating the interconnection of system components. The drive mechanism itself comprises three separate devices connected via an electronic link, while the 3-axis (X-Y-Z) Controller 201 maintains all elements in full synchronization. Each of the three driving mechanisms includes a feedback sensor.

The 3-axis motor controller 201 is set up to control three stepping motors. These are: (a) the motor 202 that controls longitudinal motion of the tubecrane; (b) the motor 203 that controls longitudinal motion of the table bucky; and (c) the motor 204 controlling x-ray tube angulation. Should one system component fail to move in the proper fashion determined by the particular mode of operation selected, the entire system, including the x-ray tube 205, will be disabled and x-ray exposure will immediately cease. Movement of each of the aforementioned system components can be detected through the use of an associated position sensor. Longitudinal position of the tubecrane is sensed by a tubecrane position sensor 209, angular position of the x-ray tube is monitored through an angular position sensor 210, and longitudinal position of the table bucky is sensed by a bucky position sensor 211. None of the moving components will contact a patient or operator during the procedure, vastly reducing the possibility of injury.

Figure 3:
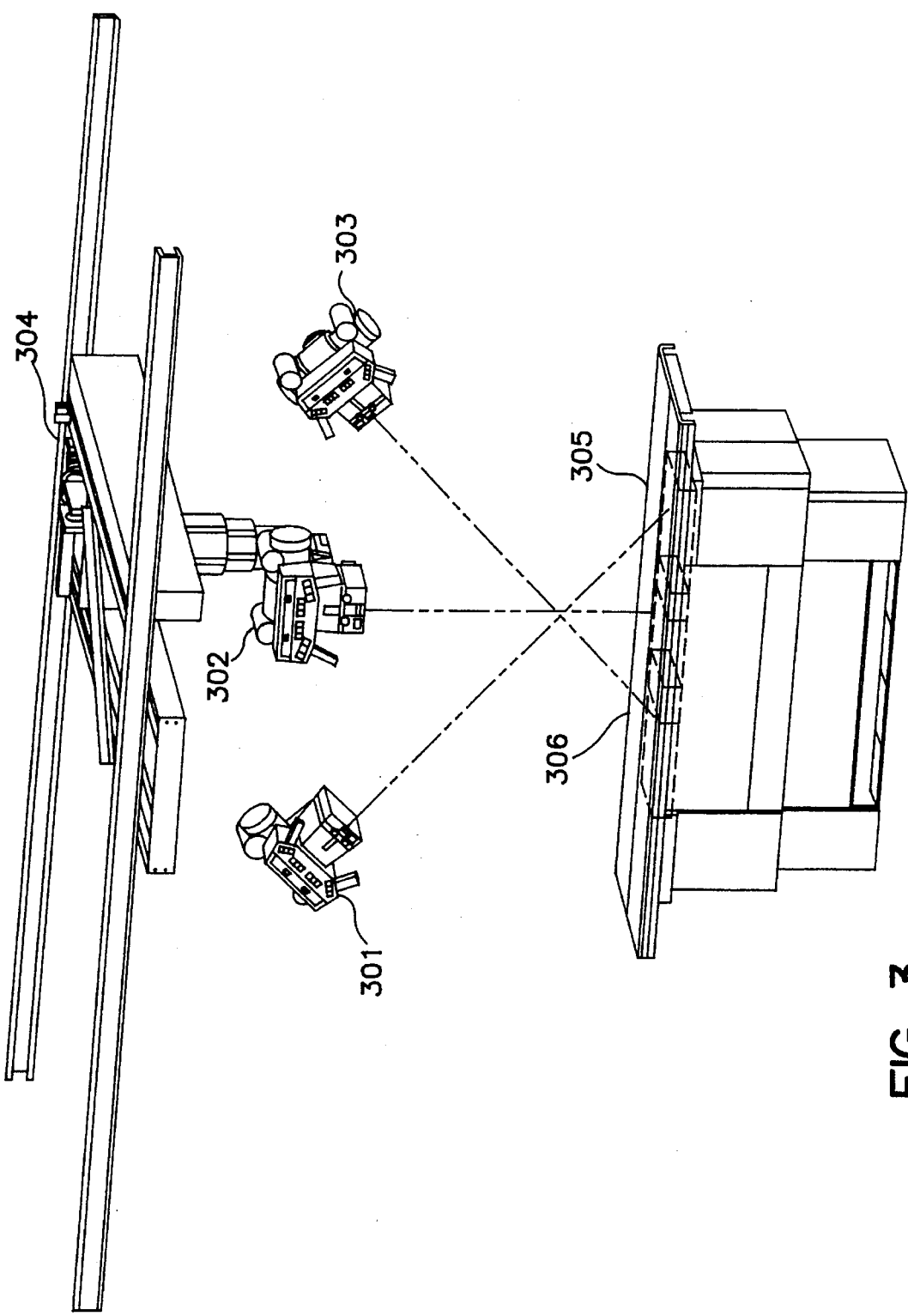
FIG. 3 is a perspective view, on a reduced scale, of linear tomographic operation.

Moving the tubecrane 206 properly is critical to proper functioning of the system, especially when linear tomographic mode has been selected. Turning briefly to FIG. 3, the tomographic mode of operation is illustrated. The x-ray tube moves from left to right, as illustrated by successive positions 301 through 303, by longitudinal movement of the tubecrane. At the same time, x-ray tube angulation is varied so that the tube always aims at the same point on the table bucky, which simultaneously traverses from right to left as illustrated by successive bucky positions 305 and 306. In order to accomplish smooth and reliable motion, a timing belt is provided to move the tubecrane during tomographic operation. This method of tubecrane drive assures the accuracy, repeatability, and reliability needed for linear tomographic operation. A stepping motor is utilized to ensure precise control of tubecrane movement. The stepping motor, manipulated by one of the axis controllers of the X-Y-Z controller, controls, synchronizes, and monitors tubecrane motion.

Control of x-ray tube angulation is also critical to proper operation. The angulation of the x-ray tube 205 appears to an observer to be slow motion. It is chain driven by a stepping motor controlled by another of the axis controllers of the X-Y-Z controller 201. The X-Y-Z controller 201 controls, synchronizes, and monitors the tube angulation motion. Just as in the control of the tubecrane 206, this method assures the accuracy, repeatability, and reliability needed for linear tomographic operation.

Of course, it is also essential in linear tomographic mode to control movement of the table bucky 207 within the radiographic examining table 212, and to synchronize this movement with tubecrane motion as well as tube angulation. The table bucky 207 is driven by a stepping motor via a rack and pinion device. The rack and pinion device is, in turn, driven by a stepping motor that is controlled by yet another axis controller of the X-Y-Z controller 201.

If an elevating examining table 212 were used, it may also be necessary to monitor the table's vertical position through an appropriate position sensor 213. In tomographic mode of operation, system component positions are monitored through the tomo control module 217, and the x-ray generator control 218 controls the points during the tomographic sweep at which x-ray exposure begins and ends.

For conventional radiographic examination in WALL MODE, a wall bucky 208 secured to a wall bucky stand 214 is used for support of radiographic media. The system as described includes a vertical position sensor 216 for the wall bucky 208.

Figure 4:
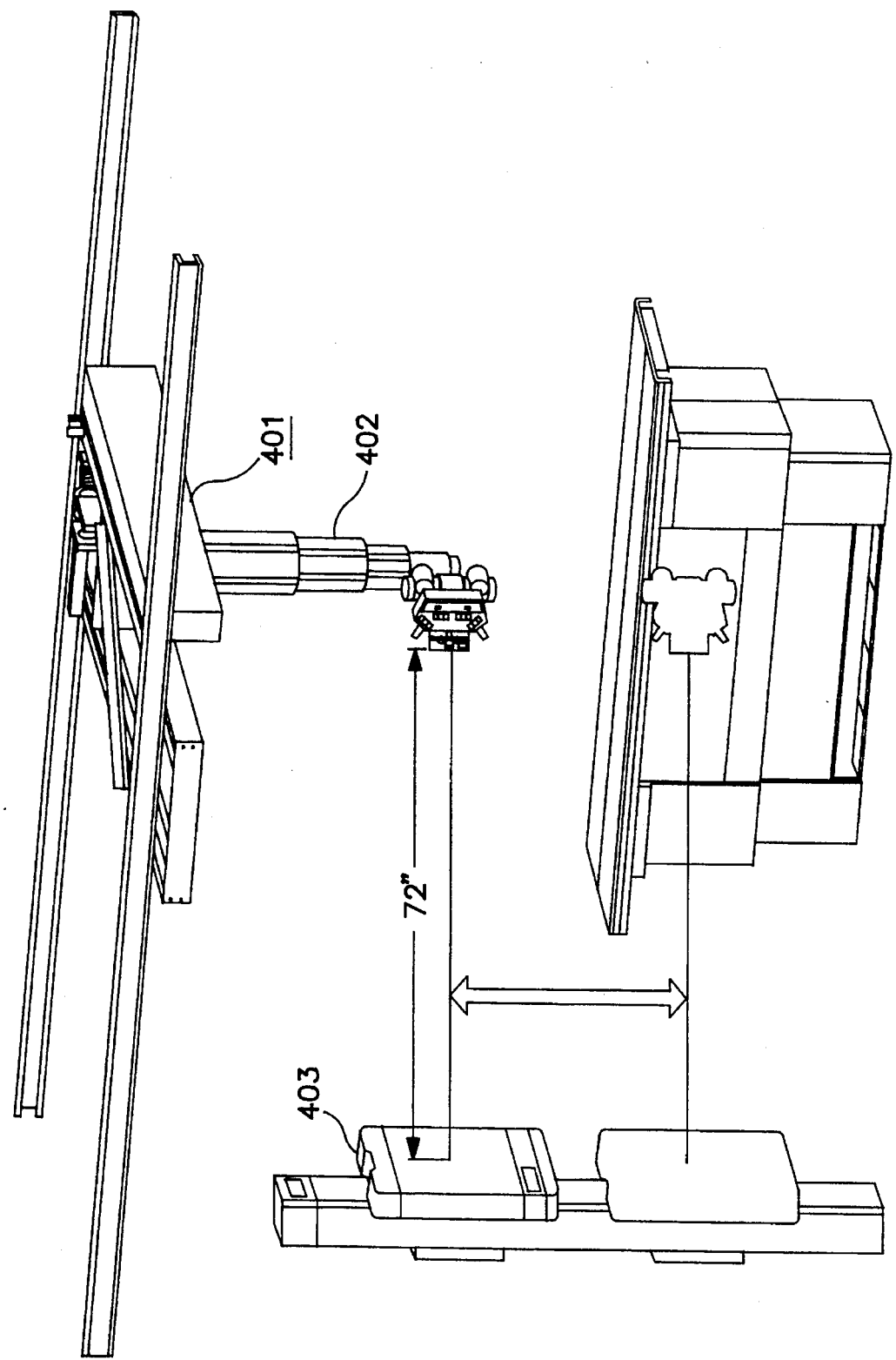
FIG. 4 is a perspective view, on a reduced scale, of WALL MODE radiographic operation in accordance with the present invention.

As mentioned above, the system supports a conventional radiographic "chest mode" using a wall bucky. For this "Chest System" mode, illustrated in FIG. 4, the tubecrane 401 (or tubestand) requires motorized vertical travel. A small gear motor is used to drive the main shaft 402 of the tubecrane. This is possible because the weight of the x-ray tube and collimator are well balanced, and only a small force is needed to move the tubecrane up and down. An electromagnetic clutch couples this small gear motor and its driving mechanism, so the mechanism can be disconnected in the manual mode. In fact, the system will remain in manual mode unless all of the following conditions are met:

a) WALL MODE is selected;
b) AUTO MODE is ON;
c) The tube is rotated 90° toward the wall bucky 403;
d) The tubecrane is in proper longitudinal SID (source-image distance) position; and
e) The tubecrane is in proper lateral position.

The electromagnetic clutch mentioned previously will slip when a force greater than about 20 pounds is applied.

Figure 5:
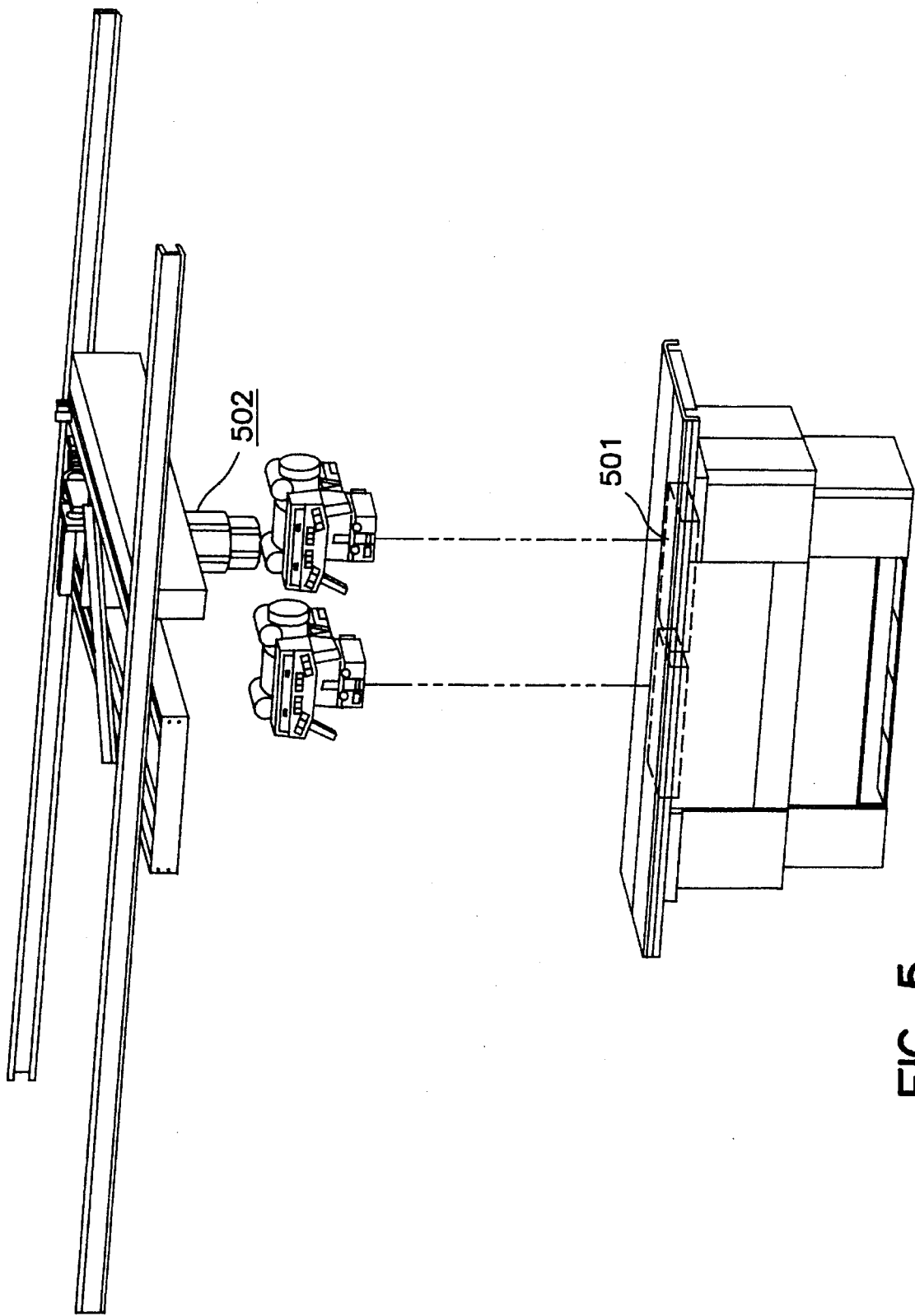
FIG. 5 is a perspective view, on a reduced scale, of BUCKY MODE radiographic operation in accordance with the present invention.

The system supports several automatic table modes that provide features very useful in conventional radiographic operation. First, there is an auto bucky mode, where the x-ray tube returns to its 0° position, with the tubecrane and table bucky aligned. In this mode, shown in FIG. 5, the table bucky 501 follows the longitudinal position of the tubecrane 502 and maintains their proper alignment, as long as the x-ray tube position is in the table bucky range. The system will remain in manual mode unless all of the following conditions are met:

a) TABLE MODE is selected;
b) AUTO MODE is ON;
c) The tube is at its 0° position;
d) The tubecrane is longitudinally in the table's bucky operation position; and
e) The tubecrane is in proper lateral position.

Figure 6:
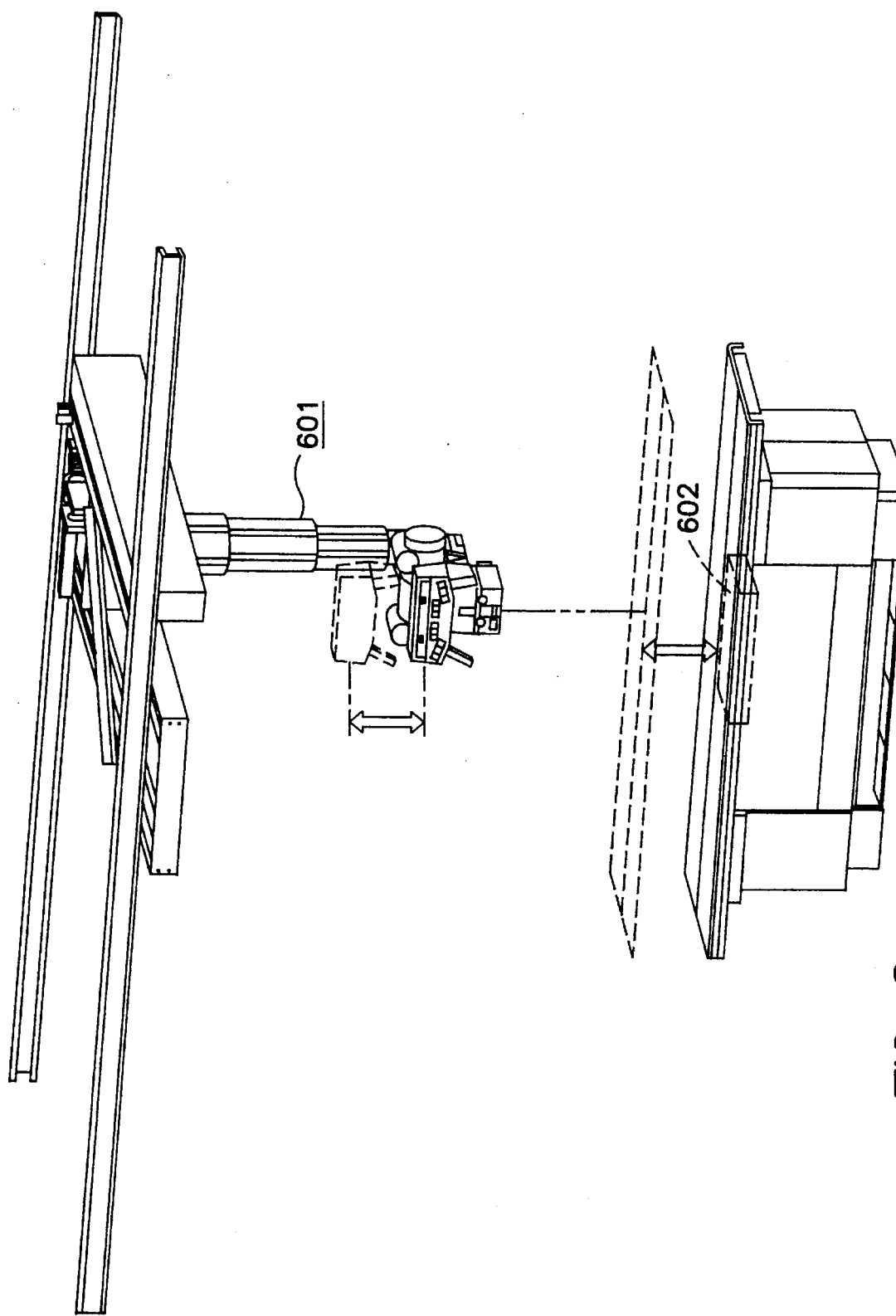
FIG. 6 is a perspective view, on a reduced scale, of TABLE MODE radiographic operation in accordance with the present invention.

The system additionally supports an AUTO TABLE MODE, illustrated in FIG. 6, in which the tubecrane 601 automatically follows the vertical position of the table bucky 602 to maintain a 40-inch vertical SID. The x-ray tube returns to its 0° position, and the tubecrane and table bucky are aligned. The system remains in a manual mode of operation unless all of the following conditions are met:

a) TABLE mode is selected;
b) AUTO MODE is ON;
c) The tube is at its 0° position;
d) The tubecrane is longitudinally in the table's bucky operation position; and
e) The tubecrane is in proper lateral SID position.

Figure 7:
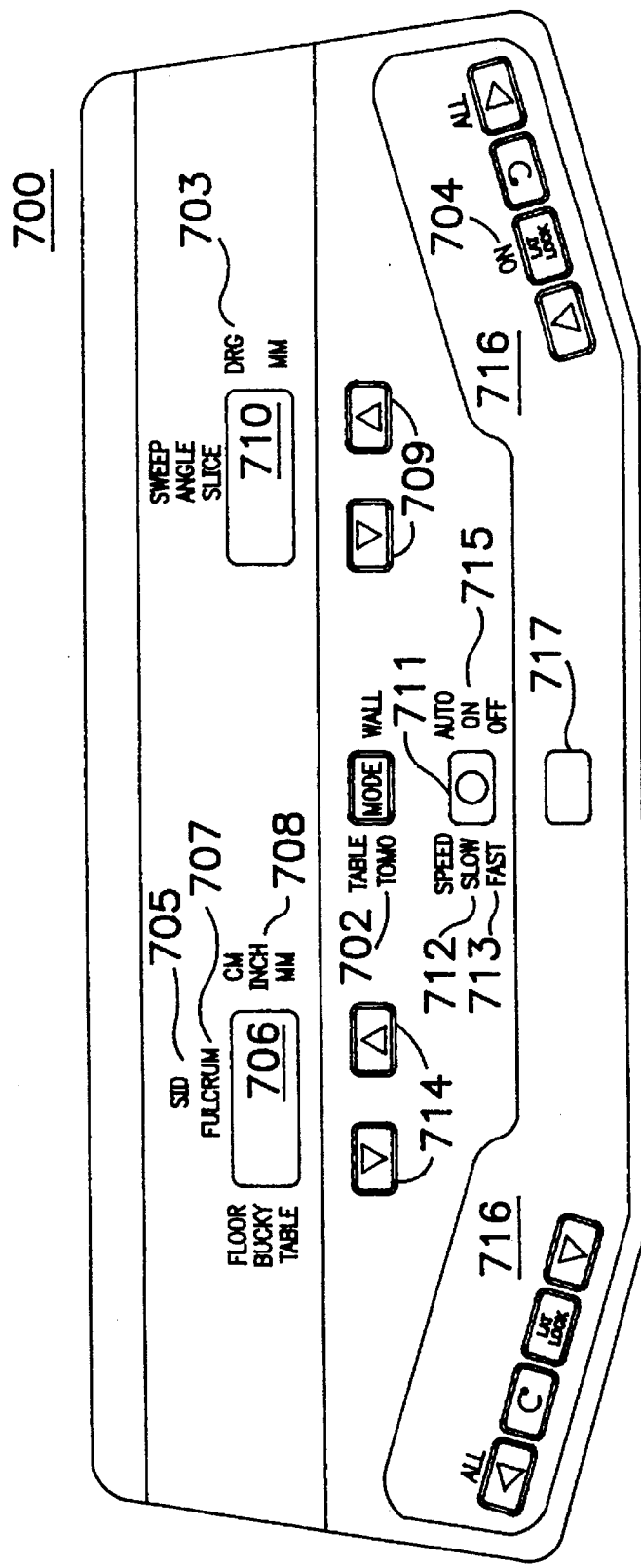
FIG. 7 is a front elevational view of a universal control panel in accordance with the present invention.

A Universal Control Panel is shown in FIG. 7, generally depicted by the numeral 700. The Universal Control Panel 700 is located on the Tubecrane/Tubestand and controls the different modes of operation, such as table top (TABLE), wall bucky (WALL) and linear tomography (TOMO). The MODE switch 701 selects or deselects TABLE, WALL or TOMO functions. The selected mode determines the functions for the rest of the controls and indicators on the control panel 700. The corresponding "dead front" backlight indicators appear when the proper mode of operation is selected.

When the TOMO MODE is selected, the x-ray tube returns to its 0° position, the tubecrane and bucky are centered, and the tubecrane is positioned at 40" SID. TOMO MODE may also be selected from the X-Ray Generator Control, by pressing the TOMO switch. The "dead front" TOMO indicator 702 will be illuminated when TOMO MODE is selected. All TOMO MODE controls will also be activated and illuminated. In the linear tomographic mode of operation, various system switches and indicators take on special significance as described in the following paragraphs.

When an attempt is made to select TOMO MODE via the MODE switch 702, all required conditions must be met or corresponding indicator(s) will blink, to indicate an error. For example, if an attempt is made to select TOMO MODE, and the x-Ray tube is not at its 0° position, both TOMO 702 and DEG 703 will blink. If the tubecrane is not laterally centered, both TOMO 702 and LAT CNTR ON indicators 704 will blink. If the tubecrane is not at its 40" SID position, the SID indicator 705 will blink, and the SID display 706 will show the actual SID in inches, until a 40" SID is achieved. At this point, the display 706 will change to the FULCRUM 707 mode and the MM indicator 708 will be illuminated. The generator's control display will indicate the same error condition.

A set of pushbutton switches 709 under the angle display 710 are used to select the tomography angle. By toggling these switches, sweep angles of 8°, 20°, 30°, or 40° will be selected, and the corresponding angle will be displayed on the 2-digit 7-segment ANGLE display 710. The backlighted DEG indicator 703 will appear on the side of the digital display 710. The approximate relationships between sweep angle and slice thickness are illustrated in the following table:

| SWEEP ANGLE | THICKNESS |
|---|---|
| 8° | 10 mm |
| 20° | 3.2 mm |
| 30° | 2.6 mm |
| 40° | 2.0 mm |

The SPEED switch 711 selects SLOW or FAST tomographic speeds. The corresponding SLOW 712 or FAST 713 message appears on the normally "dead fronted" display.

The FULCRUM 707 indicator is a 3-digit 7-segment display 706. The fulcrum distance in mm appears on the left side of the display with the last fulcrum setting entered becoming the default value.

The FULCRUM ▲/▼ controls 714 allow the operator both to increase and decrease the fulcrum level in 1 mm Increments. It will electronically select the focal plane pivot point up or down. The range of the fulcrum display 706 is 0 to 250 mm. When the ▲/▼ buttons 714 are depressed and held down, the fulcrum display 706 will begin incrementing or decrementing slowly in 1 mm steps, gradually increasing the rate of change. The entire fulcrum range can be traversed in three to four seconds.

The AUTO ON/OFF indicator 715 is used to show whether automatic or manual mode of fulcrum increments is in operation. The last setting becomes a default. If AUTO MODE is set up during installation of the generator, the AUTO display becomes available on the Universal Control Panel and AUTO ON or OFF will be illuminated. The installer will also select direction of the Fulcrum change UP or DOWN, and the increment size for each step. When tomographic mode is selected (TOMO ON), the fulcrum height is incremented after each exposure in predetermined steps for the number of steps selected for the procedure.

The lower section of the universal control panel includes the motion control switches 716. From left to right, the functional descriptions of the motion control switches 716 are as follows:

◄—Longitudinal LEFT

↶—Rotation CW

LAT LOCK—Momentary switch that releases lateral locks

▲—Vertical UP

Infrared window—for IR (infrared) remote control

▼—Vertical DOWN

LAT CNTR—ON/OFF switch, enables lateral center sensing

↷—Rotation CCW

►—Longitudinal RIGHT

If both ◄ and ► are depressed simultaneously, ALL motions will be enabled (longitudinal, transverse and vertical. It is the equivalent of "manual" vs. "motorized" motion.

If both ↶ and ↷ are depressed simultaneously, the rotation motor is "disarmed" and manual rotation motion will be enabled. It is a momentary function and is enabled only so long as both switches are depressed.

Figure 8:
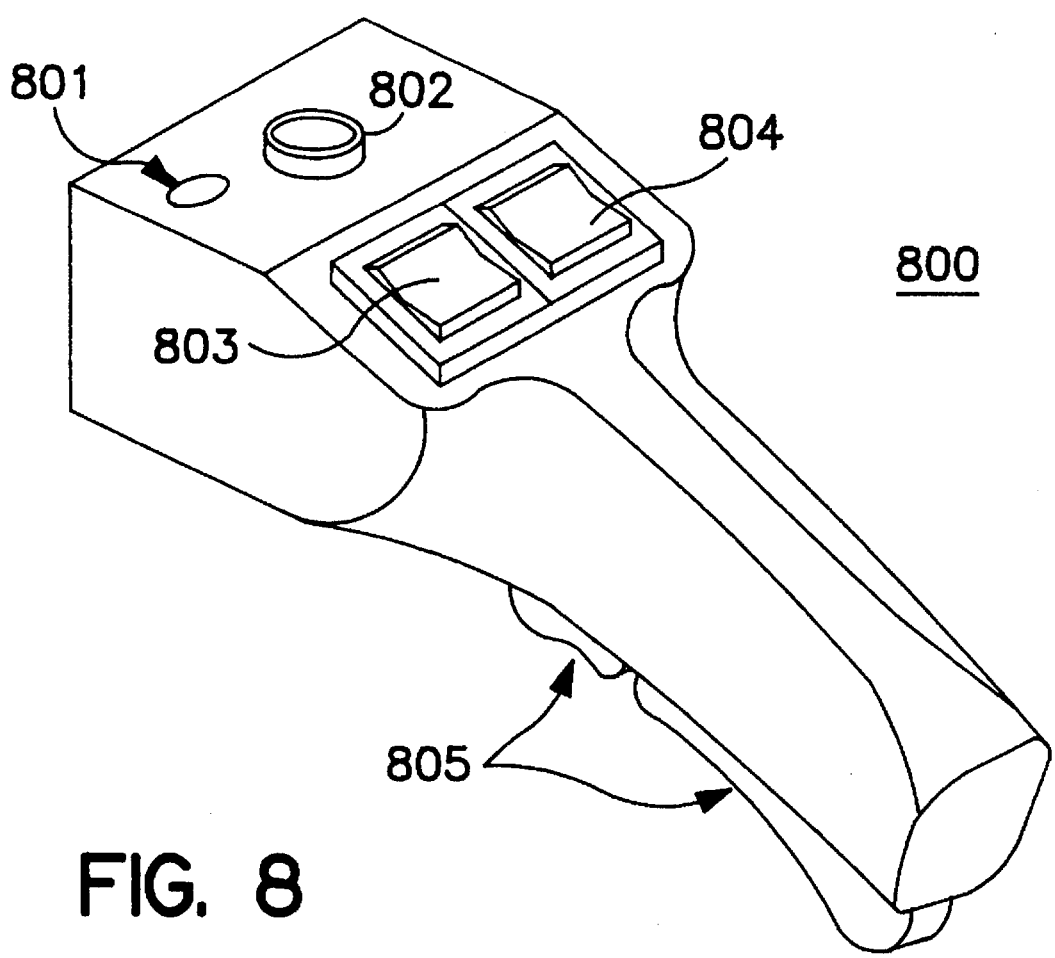
FIG. 8 is a perspective view, on a reduced scale, of a remote tomographic mode control switch in accordance with the present invention.

A Remote Tomo Control Switch is also provided, and is generally depicted by the numeral 800 in FIG. 8. The Remote Tomo Control Switch 800 provides the following control functions:

ENABLE TRIGGERS 805—enable CENTER, HOME, and TEST functions

CENTER 802—automatically longitudinally centers the tubecrane and bucky

HOME 803—moves the tubecrane to the HOME (Head End, for example) position and positions the x-ray tube and bucky for the beginning of a linear tomographic sweep TEST 804—test tomographic sweep runs The Remote Tomo Control Switch 800 is provided in two different configurations. In one configuration, the Remote Tomo Control Switch is hard wired to the Tomo Control Module. In another configuration, as mentioned briefly above, the Remote Tomo Control Switch communicates with the Universal Control Panel via an infrared link.

Perhaps the conventional radiographic mode of operation that is most frequently used by practitioners is TABLE MODE. When TABLE MODE is selected via the MODE switch, the x-ray tube returns to its 0° position, and the tubecrane and bucky are centered. The ANGLE indicator displays actual x-ray tube angulation, and the DEG indicator is illuminated. In this mode of operation, the pushbutton switches under the ANGLE display are not active.

The SID indicator is a 3-digit 7-segment display. The INCH or CM units indicator that appears on the left side of the display will illuminate to reflect whether metric or English units are selected on the Tomo Control Board at installation time.

The SID ▲/▼ control allows the operator to toggle the SID distance to be measured from the floor, bucky or table top. The motion control switches have the same functionality as described above with reference to TOMO mode. The AUTO ON/OFF control selects automatic or manual mode of operation. When AUTO MODE is ON, the bucky position follows the tubecrane position (AUTO BUCKY Mode) and the tubecrane follows the elevating table to maintain 40" SID distance (AUTO TABLE Mode). This mode of operation will be engaged only when the tube is at 0° and centered laterally.

When WALL MODE is selected via the MODE SWITCH, and the x-ray tube is not at its 90° position, the tube automatically returns to 90°. In WALL MODE, the ANGLE display indicates actual x-ray tube angulation, and the DEG indicator is illuminated. WALL MODE chest system operation will be activated only if the x-ray tube is aimed at the wall bucky, thus having an angulation of 90°. The pushbutton switches under the display are not active in this mode.

The SID indicator (described previously as a 3-digit 7-segment display) operates to display the longitudinal SID from the tube to the wall bucky. The INCH indicator appears on the left side of the display. In the preferred embodiment, WALL MODE chest system operation can only be activated if the SID is 72", although other SID's could be made available.

The SID ▲/▼ switches are disabled in this mode, and the BUCKY indicator is illuminated. The AUTO ON/OFF control selects automatic or manual mode of operation for WALL MODE chest system operation, and the motion control switches have the same functions as described previously with reference to TOMO mode.

A typical tomographic acquisition sequence will now be discussed in detail. The operator selects TOMO MODE either from the generator control or from the Universal Tomo Control. Once the TOMO MODE has been selected, and the tubecrane is at its lateral center position, the system checks to see if all required conditions have been met: the x-ray tube must be at its 0° position, and the initial SID must be set at 40 inches. Of course, the controller can automatically position the system components properly for linear tomographic mode, or initial positioning may be accomplished manually using one of the following methods. First, the operator may move each component individually by selecting the appropriate control from the control panel. Second, the operator may select HOME or CENTER on the Remote TOMO Control Unit. Third, the operator may select TEST MODE on the Control Panel to make HOME and CENTER functions available. Lastly, the operator may select PREP on the Control Panel to place the system components in their proper positions. If any condition required for TOMO MODE is not met, the corresponding indicator will blink and the TOMO function will be inhibited. In addition, a specific error message will be displayed on the generator control.

The operator then selects the desired SWEEP ANGLE and speed, which automatically selects the appropriate, predetermined exposure back-up time in the x-ray generator and displays the time on the generator console. Available TOMO angles include 8°, 20°, 30°, and 40°. The last setting becomes a default setting.

Either FAST or SLOW TOMO speed can be selected from the control panel. The operator also selects the desired imaging plane by remotely driving the fulcrum pivot point to the desired height. The last setting becomes a default setting. The fulcrum height can be adjusted from 0 mm (table top) to 250 mm above the table top in 1 mm increments.

At this point, the operator may choose to demonstrate the TOMO sweep to the patient by pressing and holding the ENABLE triggers and the HOME button on the Remote Tomo Control. This will cause the tubecrane to be driven from its center position to the HOME position. The table bucky position and the angulation of the x-ray tube will change accordingly. Then, by pressing and holding the ENABLE triggers and the TEST button on the Remote Tomo Control, a test sweep will be initiated.

To initiate a linear tomographic sweep from the x-ray generator control, the operator presses and holds the PREP button. The tubecrane and table bucky are moved to their initial positions for the tomographic sweep, and the x-ray tube is positioned at the proper initial angulation. When the operator presses and holds the PREP and EXPOSE switches, the TOMO sweep begins. Once the sweep reaches the start position of the selected sweep angle, the controller signals the x-ray generator to start the x-ray exposure. Based upon the selected sweep speed, sweep angle and fulcrum height, x-ray exposure occurs that is symmetrical with respect to the center position. Once the predetermined exposure time has been reached, implying that the tube and bucky travel have reached the end of the selected sweep angle, x-ray exposure is terminated. After each tomographic exposure, the system returns to the CENTER position.

If, at any time, the operator releases the TEST, HOME, CENTER, or ENABLE controls in the TEST MODE, or the PREP or EXPOSE buttons during operation, the tomographic motion stops. To re-position the system components to the CENTER or HOME position, the corresponding buttons on the Remote Tomo Control along with the ENABLE trigger must be activated.

AUTO tomographic mode may only be selected from the control panel. The operator must also select number of steps (1 through 10), direction of fulcrum adjustment (UP or DOWN), and initial fulcrum height.

There has been described herein a universal radiographic room relatively free from the shortcomings of the prior art. It will be apparent to those skilled in the art that modifications may be made without departing from the spirit and scope of the invention. Accordingly, it is not intended that the invention be limited except as may be necessary in view of the appended claims.

What is claimed is:

1. Radiographic apparatus operable in conventional radiographic mode or linear tomographic mode at operator discretion comprising:

x-ray tube means for controllably emitting x-rays;

support means for supporting the x-ray tube means and for enabling longitudinal and vertical motion of the x-ray tube means;

x-ray tube angulation means for varying the angle of incidence of the emitted x-rays;

examining table means for supporting a patient undergoing diagnostic radiography;

table bucky means for supporting radiographic media, said table bucky means including longitudinal drive means for moving the table bucky means in a longitudinal direction;

wall bucky means for vertically supporting radiographic media; and controller means for receiving and implementing an instruction to operate the radiographic apparatus in conventional radiographic mode or linear tomographic mode, said controller means simultaneously controlling longitudinal motion, angulation of the x-ray tube means, and motion of the table bucky means when said linear tomographic mode is selected, wherein the controller means includes a multi-axis motor controller means for controlling vertical motion of the x-ray tube means, means for sensing vertical position of the wall bucky means and coordinating motion of the x-ray tube means in response thereto and a table elevation controller means for controlling vertical motion of the examining table means in coordination with motion of the x-ray tube means.

2. The radiographic apparatus of claim 1, wherein the x-ray tube means comprises an x-ray tube.

3. The radiographic apparatus of claim 1, wherein the support means comprises a tubecrane.

4. The radiographic apparatus of claim 1, wherein the support means comprises a tubestand.

5. The radiographic apparatus of claim 1, wherein the support means includes position sensor means for sensing longitudinal position of the x-ray tube means.

6. The radiographic apparatus of claim 1, wherein the x-ray tube angulation means includes stepping motor means for changing angular position of the x-ray tube means and angular position sensor means for sensing angular position.

7. The radiographic apparatus of claim 1, wherein the examining table means is an elevating examining table.

8. The radiographic apparatus of claim 1 further including longitudinal drive means comprising stepping motor means for controllably positioning the table bucky means in a longitudinal direction.

9. The radiographic apparatus of claim 8 further including longitudinal position sensor means for sensing longitudinal position of the table bucky means.

10. The radiographic apparatus of claim 1, wherein the wall bucky means further includes vertical position sensor means for sensing vertical position of the wall bucky means.

11. The radiographic apparatus of claim 1, wherein said support means also enables lateral motion of the x-ray tube means and further comprises position sensor means for sensing lateral position.

12. Radiographic apparatus operable in conventional radiographic mode or linear tomographic mode at operator discretion comprising:

x-ray tube means for controllably emitting x-rays;

support means for supporting the x-ray tube means and for enabling longitudinal and vertical motion of the x-ray tube means;

x-ray tube angulation means for varying angle of incidence of the emitted x-rays;

examining table means for supporting a patient undergoing diagnostic radiography;

table bucky means for supporting radiographic media, said table bucky means including longitudinal drive means for moving the table bucky means in a longitudinal direction along the examining table;

controller means for receiving and implementing an instruction to prepare the radiographic apparatus for conventional radiographic mode or linear tomographic mode, said controller means responsive to said instruction to adjust the longitudinal position and angulation of the x-ray tube means, and the position of the table bucky means, as appropriate for said mode.

13. A universal radiographic device comprising:

a vertically movable tubecrane including a vertical tubecrane position sensor;

x-ray tube means supported by the tubecrane;

a vertically movable examining table positioned beneath the tubecrane, the examining table including a table bucky;

control means for exercising control over vertical motion of the tubecrane; and means for sensing vertical position of the examining table and coordinating movement of the x-ray tube means in response thereto to maintain a pre-determined vertical source-image distance.

14. The universal radiographic room of claim 13 in which the pre-determined vertical source-image distance is 40 inches.

15. A universal radiographic room comprising:

a longitudinally and vertically movable tubecrane including longitudinal and vertical tubecrane position sensors;

an x-ray tube supported by the tubecrane, and associated therewith a mechanism for varying angular position of the x-ray tube, and an angular position sensor;

an examining table positioned beneath the tubecrane, the examining table including a table bucky with a longitudinal drive mechanism and a longitudinal table bucky position sensor;

a wall bucky including a vertical wall-bucky position sensor; generator control means for exercising control over longitudinal and vertical motions of the tube crane, angular motion and activation of the x-ray tube, and longitudinal motion of the table bucky;

a control panel coupled to the generator control means, the control panel including:

selection means for selecting independent motion of the tubecrane, x-ray tube, and table bucky;

selection means for selecting automatic linear tomographic sweep;

selection means for selecting first automatic radiographic mode wherein the table bucky automatically follows movement of the tubecrane;

selection means for selecting second automatic radiographic mode wherein the tubecrane automatically follows movement of the wall bucky;

selection means for selecting third automatic radiographic mode, wherein the tubecrane automatically follows movement of the elevating table to maintain 40 inches vertical SID; and display means for displaying mode of operation and tubecrane position information.

16. The universal radiographic room of claim 15, further including a remote control means coupled to the generator control means for selecting modes of operation and displaying information to an operator.

17. The universal radiographic room of claim 16, wherein the remote control is hardwired to the generator control means.

18. The universal radiographic room of claim 16, wherein the remote control is coupled to the generator control means via an infrared communication path.

19. The universal radiographic room of claim 15, wherein the examining table positioned beneath the tube crane is an elevating examining table.

20. The universal radiographic room of claim 15, wherein the generator control means allows an operator manually to position the tubecrane, x-ray generator, and table bucky.

21. Radiographic apparatus comprising:

x-ray tube means for controllably emitting x-rays;

support means for supporting the x-ray tube means and for enabling longitudinal and vertical motion of the x-ray tube means;

x-ray tube angulation means for varying the angle of incidence of the emitted x-rays;

examining table means for supporting a patient undergoing diagnostic radiography;

table bucky means for supporting radiographic media, said table bucky means including longitudinal drive means for moving the table bucky means in a longitudinal direction;

wall bucky means for vertically supporting radiographic media; and controller means for choosing conventional radiographic mode or linear tomographic mode at operator discretion, said controller means simultaneously controlling longitudinal motion and angulation of the x-ray tube means, said controller means being responsive to selection of said linear tomographic mode to further control motion of the table bucky means while said x-ray tube means emits x-rays, wherein the controller means includes a multi-axis motor controller means for controlling longitudinal and angulation motion of the x-ray tube means, means for controlling vertical motion of the x-ray tube means, means for sensing vertical position of the wall bucky means and coordinating motion of the x-ray tube means in response thereto, and a table elevation controller means for controlling vertical motion of the examining table means in coordination with motion of the x-ray tube means, and the radiographic apparatus further includes a table bucky controller means for controlling longitudinal motion of the table bucky means in coordination with motion of the x-ray tube means.

22. The radiographic apparatus of claim 21, wherein the x-ray tube means comprises an x-ray tube.

23. The radiographic apparatus of claim 21, wherein the support means comprises a tubecrane.

24. The radiographic apparatus of claim 21, wherein the support means comprises a tubestand.

25. The radiographic apparatus of claim 21, wherein the support means includes position sensor means for sensing longitudinal position of the x-ray tube means.

26. The radiographic apparatus of claim 21, wherein the x-ray tube angulation means includes stepping motor means for changing angular position of the x-ray tube means and angular position sensor means for sensing angular position.

27. The radiographic apparatus of claim 21, wherein the examining table means is an elevating examining table.

28. The radiographic apparatus of claim 21, wherein the table bucky means further includes longitudinal drive means comprising stepping motor means for controllably positioning the table bucky means in a longitudinal direction.

29. The radiographic apparatus of claim 28, further including longitudinal position sensor means for sensing longitudinal position of the table bucky means.

30. The radiographic apparatus of claim 28, further including vertical position sensor means for sensing vertical position of the wall bucky means.

31. The radiographic apparatus of claim 21, wherein the controller means further includes means for sensing vertical position of the examining table means and coordinating motion of the x-ray tube means in response thereto.

32. Radiographic apparatus operable in conventional radiographic mode or linear tomographic mode at operator discretion comprising:

x-ray tube means for controllably emitting x-rays;

support means for supporting the x-ray tube means and for enabling longitudinal and vertical motion of the x-ray tube means;

x-ray tube angulation means for varying angle of incidence of the emitted x-rays;

examining table means for supporting a patient undergoing diagnostic radiography;

table bucky means for supporting radiographic media, said table bucky means including longitudinal drive means for moving the table bucky means in a longitudinal direction;

wall bucky means for vertically supporting radiographic media; and controller means for receiving and implementing an instruction to operate the radiographic apparatus in conventional radiographic mode or linear tomographic mode, said controller means simultaneously controlling longitudinal motion, angulation of the x-ray tube means, and motion of the table bucky means, when said linear tomographic mode is selected, wherein the controller means includes a multi-axis motor controller means for controlling longitudinal and angulation motion of the x-ray tube means, and means for sensing vertical position of the examining table means and coordinating motion of the x-ray tube means in response thereto, and the radiographic apparatus further includes a table bucky controller means for controlling longitudinal motion of the table bucky means in coordination with motion of the x-ray tube means.

33. The radiographic apparatus of claim 32, wherein the x-ray tube means comprises an x-ray tube.

34. The radiographic apparatus of claim 32, wherein the support means comprises a tubecrane.

35. The radiographic apparatus of claim 32, wherein the support means comprises a tubestand.

36. The radiographic apparatus of claim 32, wherein the support means includes position sensor means for sensing longitudinal and vertical position.

37. The radiographic apparatus of claim 32, wherein the x-ray tube angulation means includes stepping motor means for changing angular position of the x-ray tube means and angular position sensor means for sensing angular position.

38. The radiographic apparatus of claim 32, wherein the examining table means is an elevating examining table.

39. The radiographic apparatus of claim 32, wherein the table bucky means includes longitudinal drive means comprising stepping motor means for controllably positioning the table bucky means in a longitudinal direction.

40. The radiographic apparatus of claim 39, wherein the table bucky means further includes longitudinal position sensor means for sensing longitudinal position of the table bucky means.

41. The radiographic apparatus of claim 32, including wall bucky means.

42. The radiographic apparatus of claim 41, wherein the controller means further includes means for sensing vertical position of the wall bucky means and coordinating motion of the x-ray tube means in response thereto.

43. The radiographic apparatus of claim 42, wherein the controller means further includes a table elevation controller means for controlling vertical motion of the examining table means in coordination with motion of the x-ray tube means.

44. Radiographic apparatus comprising:

x-ray tube means for controllably emitting x-rays;

support means for supporting the x-ray tube means and for enabling longitudinal and vertical motion of the x-ray tube means;

x-ray tube angulation means for varying the angle of incidence of the emitted x-rays;

examining table means for supporting a patient undergoing diagnostic radiography;

table bucky means for supporting radiographic media, said table bucky means including longitudinal drive means for moving the table bucky means in a longitudinal direction; and controller means for choosing conventional radiographic mode or linear tomographic mode at operator discretion, said controller means simultaneously controlling longitudinal motion and angulation of the x-ray tube means, said controller means being responsive to selection of said linear tomographic mode to further control motion of the table bucky means while said x-ray tube means emits x-rays, wherein the controller means includes a multi-axis motor controller means for controlling longitudinal and angulation motion of the x-ray tube means, and means for sensing vertical position of the examining table means and coordinating motion of the x-ray tube in response thereto.

45. The radiographic apparatus of claim 44, wherein the x-ray tube means comprises an x-ray tube.

46. The radiographic apparatus of claim 44, wherein the support means comprises a tubecrane.

47. The radiographic apparatus of claim 44, wherein the support means comprises a tubestand.

48. The radiographic apparatus of claim 44, wherein the support means includes position sensor means for sensing longitudinal position of the x-ray tube means.

49. The radiographic apparatus of claim 44, wherein the x-ray tube angulation means includes stepping motor means for changing angular position of the x-ray tube means and angular position sensor means for sensing angular position.

50. The radiographic apparatus of claim 44, wherein the examining table means is an elevating examining table.

51. The radiographic apparatus of claim 44, including wall bucky means for vertically supporting radiographic media.

52. The radiographic apparatus of claim 51, wherein the table bucky means further includes longitudinal drive means comprising stepping motor means for controllably positioning the table bucky means in a longitudinal direction.

53. The radiographic apparatus of claim 52, further including longitudinal position sensor means for sensing longitudinal position of the table bucky means.

54. The radiographic apparatus of claim 52, further including vertical position sensor means for sensing vertical position of the wall bucky means.

55. The radiographic apparatus of claim 51, wherein the controller means a multi-axis motor controller means for controlling vertical motion of the x-ray tube means, and further includes means for sensing vertical position of the wall bucky means and coordinating motion of the x-ray tube means in response thereto.

56. The radiographic apparatus of claim 55, wherein the controller means further includes a table elevation controller means for controlling vertical motion of the examining able means in coordination with motion of the x-ray tube means.

* * * * *